US006506606B1

(12) United States Patent
Winkelman et al.

(10) Patent No.: US 6,506,606 B1
(45) Date of Patent: *Jan. 14, 2003

(54) METHOD AND APPARATUS FOR DETERMINING ERYTHROCYTE SEDIMENTATION RATE AND HEMATOCRIT

(75) Inventors: James W. Winkelman, Brookline, MA (US); Milenko J. Tanasijevic, Chestnut Hill, MA (US); Michael Bennett, Cambridge, MA (US)

(73) Assignee: Brigham and Women's Hospital, Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/471,536

(22) Filed: Jun. 6, 1995

(51) Int. Cl.⁷ .................. G01N 33/49; G01N 33/86; G01N 9/30
(52) U.S. Cl. .............. 436/70; 422/72; 422/73; 436/63; 436/66
(58) Field of Search .............. 436/63, 66, 70; 422/72, 73; 494/16, 10; 73/61.65, 61.66

(56) References Cited

U.S. PATENT DOCUMENTS

| | | | | |
|---|---|---|---|---|
| 3,009,388 A | * | 11/1961 | Polanyi | 356/40 |
| 3,199,775 A | | 8/1965 | Drucker | 494/19 |
| 3,648,159 A | * | 3/1972 | Stansell et al. | 436/68 X |
| 3,679,367 A | * | 7/1972 | Negersmith et al. | 422/72 |
| 3,684,450 A | * | 8/1972 | Adller et al. | 422/72 X |
| 3,824,841 A | | 7/1974 | Bull | 436/70 X |
| 4,045,175 A | * | 8/1977 | Weber | 436/70 |
| 4,052,164 A | * | 10/1977 | König | 422/72 |
| 4,118,974 A | | 10/1978 | Nozaki et al. | 73/61.4 |
| 4,193,538 A | * | 3/1980 | Schwartz | 422/72 X |
| 4,708,940 A | * | 11/1987 | Yoshida et al. | 436/45 |
| 4,774,056 A | * | 9/1988 | Ricci et al. | 436/70 X |
| 4,822,568 A | | 4/1989 | Tomita | 422/73 |
| 4,848,900 A | | 7/1989 | Kuo et al. | 356/39 |
| 5,279,150 A | * | 1/1994 | Katzer et al. | 436/70 X |
| 5,316,729 A | * | 5/1994 | Orth et al. | 422/73 |
| 5,328,822 A | * | 7/1994 | McKinney et al. | 435/4 |
| 5,583,432 A | * | 12/1996 | Barnes | 324/204 |
| 5,594,164 A | * | 1/1997 | Bull | 73/61.66 |

FOREIGN PATENT DOCUMENTS

| | | | | |
|---|---|---|---|---|
| DE | 4116313 | * | 11/1992 | |
| FR | 1.214.144 | | 4/1958 | |
| FR | 2 435 714 | | 9/1979 | |
| FR | 263486 | * | 2/1990 | |
| JP | 59-145964 | * | 8/1984 | 436/70 |
| JP | 63-91561 | * | 4/1988 | |

OTHER PUBLICATIONS

V.V. Morariu et al, J. Biol. Phys. 1986, 14, 73–76.*
H. Wagner et al, Med. Klin. 1989, 84, 15–22. Jan. 1989.*
N. Thomas et al, New Zealand J. Med. Lab. Sci. 1993, 47, 59–61. 1993.*
J. A. Sirs Phys. Med. Biol. Jan. 1970, 15, 9–14.*

(List continued on next page.)

*Primary Examiner*—Arlen Soderquist
(74) *Attorney, Agent, or Firm*—Samuels, Gauthier & Stevens

(57) ABSTRACT

A method and apparatus is disclosed for determining the erythrocyte sedimentation rate and hematocrit simultaneously with the centrifugation of whole blood. A centrifuge separates the whole blood into its erythrocytes and its fluid portion. A video camera measures the levels of whole blood, erythrocytes and the fluid portion of the blood and records the time of the formation of an interface between the erythrocytes and fluid portion. A monitor displays the results of the recording. Also disclosed are the method steps performed.

8 Claims, 6 Drawing Sheets

J. Meyer Birmingham Univ. Chem. Eng. 1973, 24, 10–16.*

International Committee for Standardization in Haematology Am. J. Clin. Path. Oct. 1977, 68, 505–507.*

S. Marstein et al, Tidsskr Nor Laegeforen 1986, 106, 2645–2647.*

P. C. Raich et al, Am. J. Clin. Pathol. May. 1976, 65, 690–693.*

H. Wagner et al, Medline Abstract 1989, 89143297.*

W. N. Patton et al, J. Clin. Pathol. Mar. 1989, 42, 313–317.*

M. Caswell et al, J. Clin. Pathol. Nov. 1991, 44, 946–949.*

B. S. Bull et al, J. Clin. Pathol. 1993, 46, 198–203.*

D. Lerche et al. *Biorheology* 1988, 25, 245–252.*

J. W. Stewart *Bibliotheca Haematologica* 1966, 24, 101–108.*

J. A. Sirs *Biorheology* 1968, 5, 1–14.*

J. R. Pellon et al. *Rev. Esp. Fisiol.* 1981, 37, 463–468.*

D. Lerche *Biorheology* 1992, 29, 107, abstract No. F 18. 1.*

T. Dschietzig et al. *Biomed. Technik* 1994, 39, 8–12.*

M. Rampling et al. *Phys. Med. Biol.* 1970, 15, 15–21.*

S. Natelson et al. *Microchem. J.* 1973, 17, 457–485.*

D. L. Rockholt et al. *Biophys. Chem* 1976, 5, 55–75.*

B. D. Young in "Centrifugation: A Practical Approach" D. Richwood ed. 1978, pp. 93–116.*

R. Gauglitz et al. *Colloid Polym. Sci* 1989, 267, 1108–1112.*

S. Natelson et al. *Chem. Abstr.* 1973, 79, 123211h.*

M. Rampling et al. *Phys. Med Biol.* 1970, 15, 15–21.*

M. Weissel *Z. Med. Labartech.* 1972, 13, 97–116.*

S. B. Henriques *Z. Phys. Chem.* 1976, 257, 779–791.*

K. Heinritzi et al. *Prakt. Tierarzt* 1981, 62, 972–974.*

U. Klodwig et al. *Colloid Polym. Sci.* 1989, 267, 1117–1126.*

M. Brabetz et al. Schweiz. Rundschau Med. (Praxis) 1994, 83 1034–1038.*

U. Sedlack et al. *Prog. Colloid Polym. Sci.* 1995, 99, 136–143.*

T. Dschietzig et al., "Sedimentation Analyser—Calibration and Testing of a New Device for Recording the Separation Behaviour of Blood and Other Dispersed Systems", *Biomedizinische Technik Band* 39: 8–12 (1994).

* cited by examiner

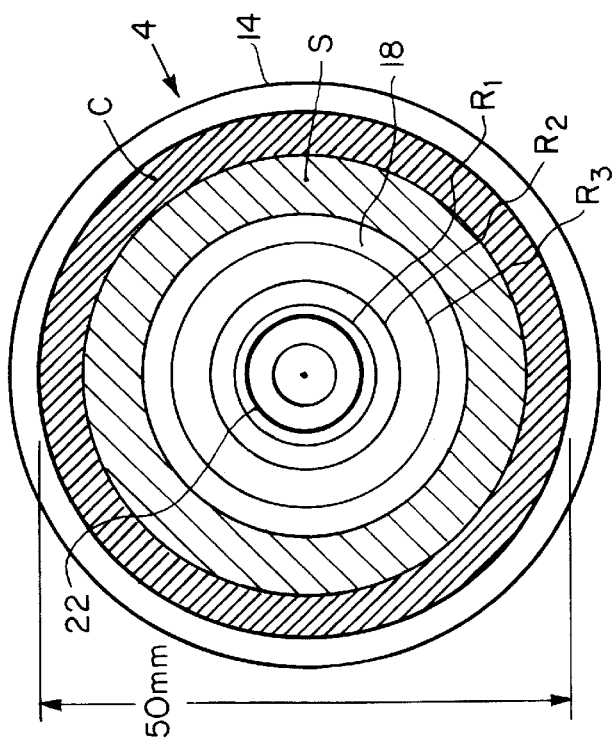
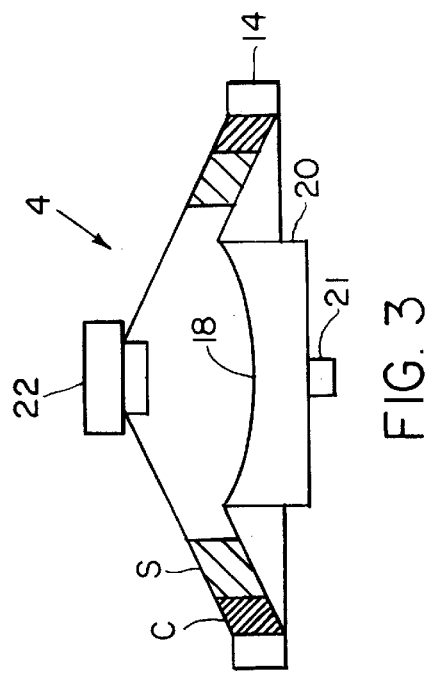
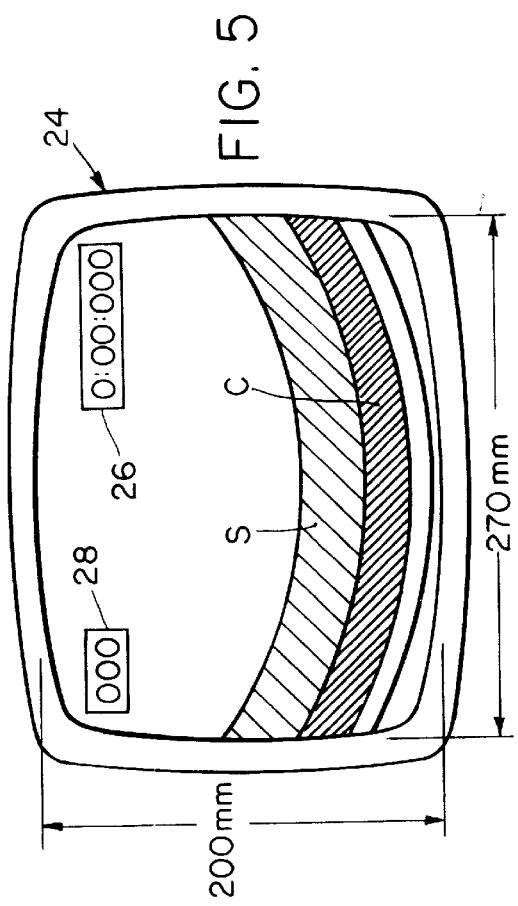

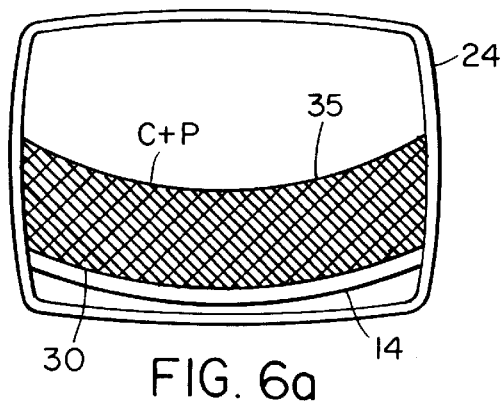
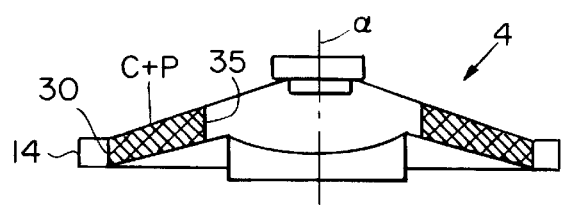
FIG. 6a  FIG. 6b
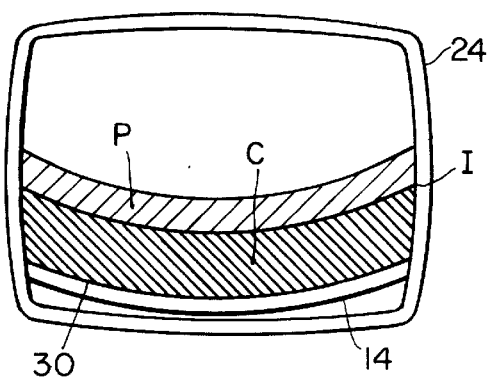
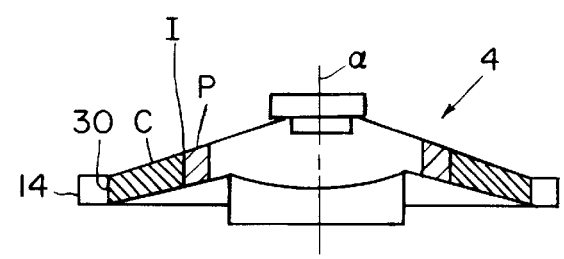
FIG. 7a  FIG. 7b
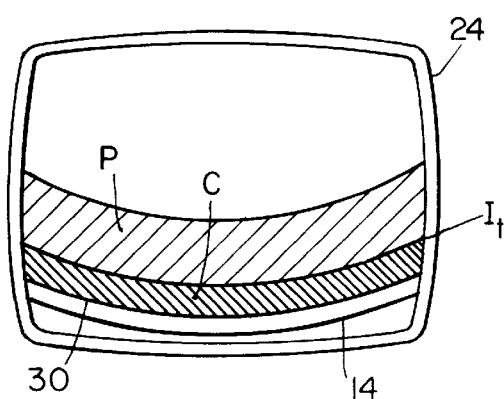
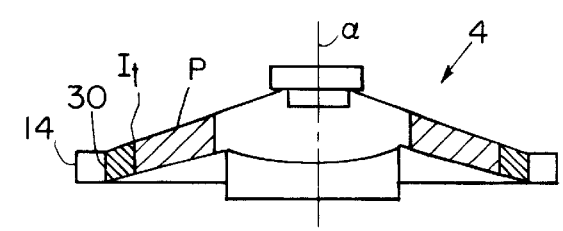
FIG. 8a  FIG. 8b

METHOD AND APPARATUS FOR DETERMINING ERYTHROCYTE SEDIMENTATION RATE AND HEMATOCRIT

BACKGROUND OF THE INVENTION

Daily there are hundreds of thousands of samples of blood drawn in hospitals, medical clinics and doctors' offices for analytical purposes. Some of this blood is analyzed directly as whole blood without being processed. Some is analyzed after separation of the cellular components of the blood (e.g., leukocytes and erythrocytes) from the fluid portion of the blood (plasma or serum).

For example, whole blood can be used for hematological analysis to measure the total concentration of red blood cells and white blood cells in the whole blood, or to prepare blood smears for microscopic analysis of the different types of cells that are present in the blood. Microscopic analysis can be used to diagnose a number of different diseases that might be present, such as certain types of leukemias or anemias. Very commonly, the patient will have a complete blood count (CBC) performed on a whole blood sample. A CBC typically includes a red blood cell (RBC) count, a white blood cell (WBC) count, a differential white blood cell count to identify the types of white blood cells present, a platelet count and the determination of blood parameters such as total hemoglobin and hematocrit.

Alternatively, whole blood can be processed to separate the cellular components from the fluid portion to obtain serum or plasma. Initially, blood is drawn from a patient into a small glass tube. If the tube contains an anticoagulant, the blood does not coagulate (i.e., form a clot) and the cells remain "suspended" in the plasma. If the tube does not contain an anticoagulant, the blood coagulates. The formation of a clot removes certain protein components from the plasma, with serum remaining as the fluid portion of the blood. Processing whole blood to separate cells from plasma/serum is typically accomplished by centrifugation.

Analysis of other physiological parameters can be performed on the plasma or serum, per se, which contain extracellular components such as proteins, hormones and electrolytes. A patient undergoing a general physical examination will probably have tests performed on both serum and plasma.

Erythrocyte sedimentation rate (ESR) is one of the traditional tests performed on whole blood in hematology laboratories. ESR measures the distance red blood cells sediment, or fall, in a vertical tube over a given period of time. The measurement of sedimentation is calculated as millimeters of sedimentation per hour and takes greater than one hour to complete. The principle behind ESR is that various "acute phase" inflammatory proteins can affect the behavior of red blood cells in a fluid medium (e.g., decrease the negative charge of RBCs). Inflammatory proteins, such as fibrinogen, will typically appear in the blood, or increase in concentration, during inflammatory processes, such as arthritis. The result is decreased negative charge (zeta-potential) of the erythrocytes that tends to keep them apart, and a more rapid fall of the cells in the analysis tube. The greater the fall of red blood cells in the vertical tube measured at a given period of time, the higher the ESR. A high (i.e., elevated) ESR is indicative of the presence of inflammatory proteins, (i.e., an active inflammatory processes, such as rheumatoid arthritis, chronic infections, collagen disease and neoplastic disease).

The process of collecting the blood specimen and the particular anticoagulant used are crucial in determining an accurate ESR. For example, in one well-known technique known as the Westergren method, blood is collected in the presence of the anticoagulant, sodium citrate, whereas in the modified Westergren procedure, EDTA is used as the anticoagulant. The modified Westergren procedure has become the standard for measuring ESR because it allows the ESR to be performed from the same tube of blood as is used for hematologic studies. Essentially, ESR is a test that has been practiced for decades without much change in the procedure.

Hematocrit (HCT) or packed red blood cell volume is the ratio of the volume of red blood cells (expressed as percentage or as a decimal fraction) to the volume of whole blood of which the red blood cells are a component. In the micromethod for determining hematocrit, tubes containing whole blood are centrifuged for 5 min at 10–12000 g to separate the whole blood into red cells and plasma. The hematocrit is calculated from the length of the blood column, including the plasma, and the red cell column alone, measured with a millimeter rule. One of the problems with this technique is that it's time consuming and erroneous results may occur as a result of incorrect reading of the levels of cells and plasma or if a significant concentration of plasma becomes trapped within the red cell layer.

It is an object of this invention to measure both erythrocyte sedimentation rate and hematocrit simultaneously with the centrifugation of the whole blood specimen, which is performed for other purposes. In other words, the object is to obtain two critically important blood parameters during the routine centrifugation that is almost universally performed on every blood sample drawn for analytical purposes, without additional manipulation or handling of the blood sample.

Another object is to perform these determinations as rapidly as possible, and have results available much faster than with currently practiced methods.

SUMMARY OF THE INVENTION

The invention resides in a method of calculating the erythrocyte sedimentation rate and hematocrit simultaneously with the centrifugation of whole blood for other purposes and apparatus for performing the method.

A sample of whole blood is collected in a container in the presence or absence of an anticoagulant. With the dimensions of the container known, the volume is ascertainable by the blood's level in the container. Thus, the blood level relative to a fixed point in the container need only be measured. A sample is centrifuged to create an interface between the erythrocytes and the plasma or serum. The location of the interface relative to a fixed point in the container is measured as well as the elapsed time between initiating the centrifugation of the blood and the time the interface between the erythrocytes and the plasma or serum is formed. The time and dimensional factors are measured optically and permanently recorded. The erythrocyte sedimentation rate of the sample is calculated from the elapsed time and the hematocrit of the sample is calculated from the difference between the two measured locations.

The step of measuring the location of the original sample, the interface and the elapsed time of forming the interface is performed by a video camera which records on tape and which is monitored by a video monitor.

A chart comparing the results of measuring erythrocyte sedimentation rate by standard known techniques and that obtained by the above-described method was made to show the correlation of the two techniques. Thereafter, the chart may be referred to in order to obtain erythrocyte sedimentation rate expressed in millimeters per hour (conventional manner) from a measurement of the elapsed time (expressed in seconds) for interface formation.

The above and other features of the invention including various and novel details of construction and combination of parts will now be more particularly described with reference to the accompanying drawings and pointed out in the claims. It will be understood that the particular method and apparatus for determining erythrocyte sedimentation rate and hematocrit embodying the invention is shown by way of illustration only and not as a limitation of the invention. The principles and features of this invention may be employed in varied and numerous embodiments without departing from the scope of the invention.

BRIEF DESCRIPTION OF THE DRAWINGS

FIG. 2 is a top plan view on enlarged scale of a centrifuge rotor employed with the apparatus.

FIG. 3 is a partial sectional view of the rotor shown in FIG. 2.

FIG. 4 is a detail sectional view of the rotor on a smaller scale.

FIG. 5 is a front view of a video monitor employed with the apparatus.

FIG. 6a is a view of the monitor showing a blood sample before centrifugation.

FIG. 6b is a schematic showing of the rotor 4 corresponding to FIG. 6a with the blood sample before centrifugation.

FIG. 7a is a view of the monitor showing the blood sample during centrifugation.

FIG. 7b is a schematic showing of the rotor 4 corresponding to FIG. 7a showing the blood sample during centrifugation.

FIG. 8a is a view of the monitor after the erythrocytes and plasma have been separated.

FIG. 8b is a showing of the rotor 4 corresponding to FIG. 7a after the erythrocytes and plasma have been separated.

DETAILED DESCRIPTION OF THE INVENTION

Figure 1:
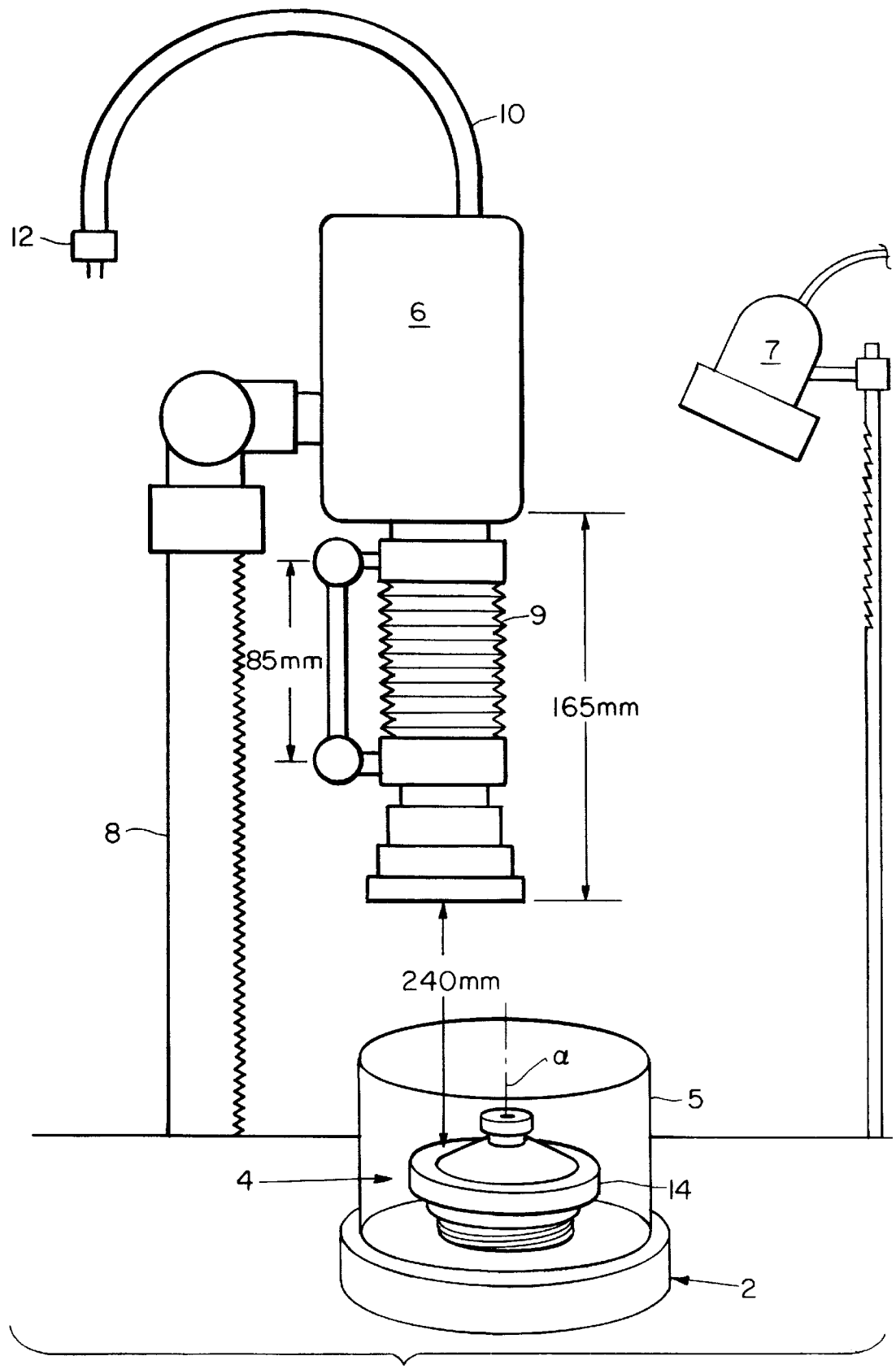
FIG. 1 is a schematic showing of apparatus for determining erythrocyte sedimentation rate and hematocrit by optical measurement.

Referring to FIG. 1, apparatus is schematically illustrated for determining sedimentation rate of whole blood simultaneously with centrifuging blood for other purposes. A small, high-speed, bench top centrifuge 2 mounts a rotor 4 within a transparent shield 5 for rotation on a vertical axis α. One such centrifuge is sold under the name Stat-Spin® by StatSpin Technologies of Norwood, Mass. A high speed video camera designated NAC HSV-300 is mounted for vertical adjustment on a stand 8. A continuous light 7 is mounted to project on the rotor 4. An output cable 10 of the camera having a plug 12 leads to a video tape recorder (not shown) and a monitor 24 seen in FIGS. 5 to 8b.

Secured to the video camera 6 is a lens extension bellows 9, made by the Nikon Company and designated PB-6E. On the forward or lower end of the bellows is a 105 mm f.1.8 Nikkor lens. During testing, the bellows was set with an 85 mm extension. The lens, through the bellows extension, was 165 mm from the shutter of the video camera 6. The front element of the lens was positioned 240 mm from the centrifuge rotor 4.

The rotor 4 will be seen in more detail in FIG. 4. It is a commercial, circular rotor also made by Stat-Spin Technologies and includes an outer circular flange or rim 14 tapering downwardly and outwardly as viewed in FIG. 4 from a central conical portion 16 having a concave bottom 18. The interior of the flange ends at a circular wall 30. The rotor fits on a rotor holder 20 secured by an expandable rubber "O" ring 19. A downwardly, extending projection 21 of the holder 20 secures the rotor holder in the body of the centrifuge 2. The central uppermost portion of the rotor 4 is plugged with a removable stopper 22 (FIG. 3).

The video monitor 24 as shown in FIG. 5 is of a standard commercially available type measuring 270 mm wide and 200 mm high. A time code window 26 appears in the upper right hand corner of the screen of the monitor 24 and a specimen identification window 28 is in the upper left hand corner.

Two hundred samples of whole blood from actual hospital patients were analyzed by the conventional modified Westergren technique. A one ml aliquot from each of the prepared whole blood samples was pipetted into its own separate plastic rotor 4 of the type shown in FIGS. 3 and 4. Each rotor was, in turn, loaded onto the bench top centrifuge 2. The high speed video camera 6 and the strobe light 7 were turned on and centrifugation begun. For each sample, the rotor 4 was spun at 3,500 rpm and the samples were continuously illuminated. The video camera recorded at 200 frames/sec with 1/200 sec exposure time. The elapsed time in seconds of rotation for each sample was recorded on the video tape within the camera 6 and shown in the time code viewer 26. The time required for the plasma and the red blood cells to form an interface was obtained from the readout of the time code window 26 and by viewing the video tape played back in slow motion. The results were recorded by sample-by-sample as will be described in greater detail hereinafter.

As can be seen in FIGS. 6a–8b, the relationship between the whole blood (hereinafter designated C+P for cells plus plasma) in the rotor 4 relative to the view on the monitor (and thus the tape) is illustrated. Initially, the whole blood sample was collected in the presence of an anticoagulant, well mixed and placed in the rotor 4. It is shown cross-hatched in FIG. 6a and 6b. It forms a uniform ring against the inner circular wall 30 of the rotor. The opposite circular edge or height of the blood sample is designated 35. The whole blood appears on the monitor screen as a single wide curved band, designated C+P in FIG. 6a and extending from circular band 35 to circular band 30.

As seen in FIGS. 7a and 7b, in the initial phase of separation, an interface I begins to form between the blood cells C and the plasma P. In other words, the red blood cells C begin moving away from the plasma P.

The interface I migrates progressively outwardly of the axis α of the rotor 4 toward the circular inner wall 30 of the rotor 4. However, when all of the cells C have been separated from the plasma P, the interface I between the cells C and the plasma P reaches a terminal point $I_t$ seen on the screen as a curved line between the bands of plasma P and the cells C. The elapsed time between the initial start of the centrifugation and the time to complete separation ($I_t$) is determined by the operator reading the time code on the video monitor 26. It is also permanently recorded on the tape for future reference. The actual time of the complete migration of the cells from the plasma was subsequently checked by viewing the video tape in slow motion in the playback mode.

The formation of the terminal interface $I_t$ between the plasma P and the blood cells C was found to be completed within the first 20–45 seconds of centrifugation at 3,500 rpm.

Of the two hundred samples of blood, the ESR of a portion of each sample was measured by the conventional modified Westergren method and of another portion by elapsed time measured as described above. The results for each sample were plotted as will be seen in FIG. 9. The time required for the interface formation in the centrifuge inversely correlated with the ESR obtained by the modified Westergren method. The study indicated that measuring ESR by the centrifugation method was not only simpler but much quicker than measuring by the modified Westergren method.

Figure 9:
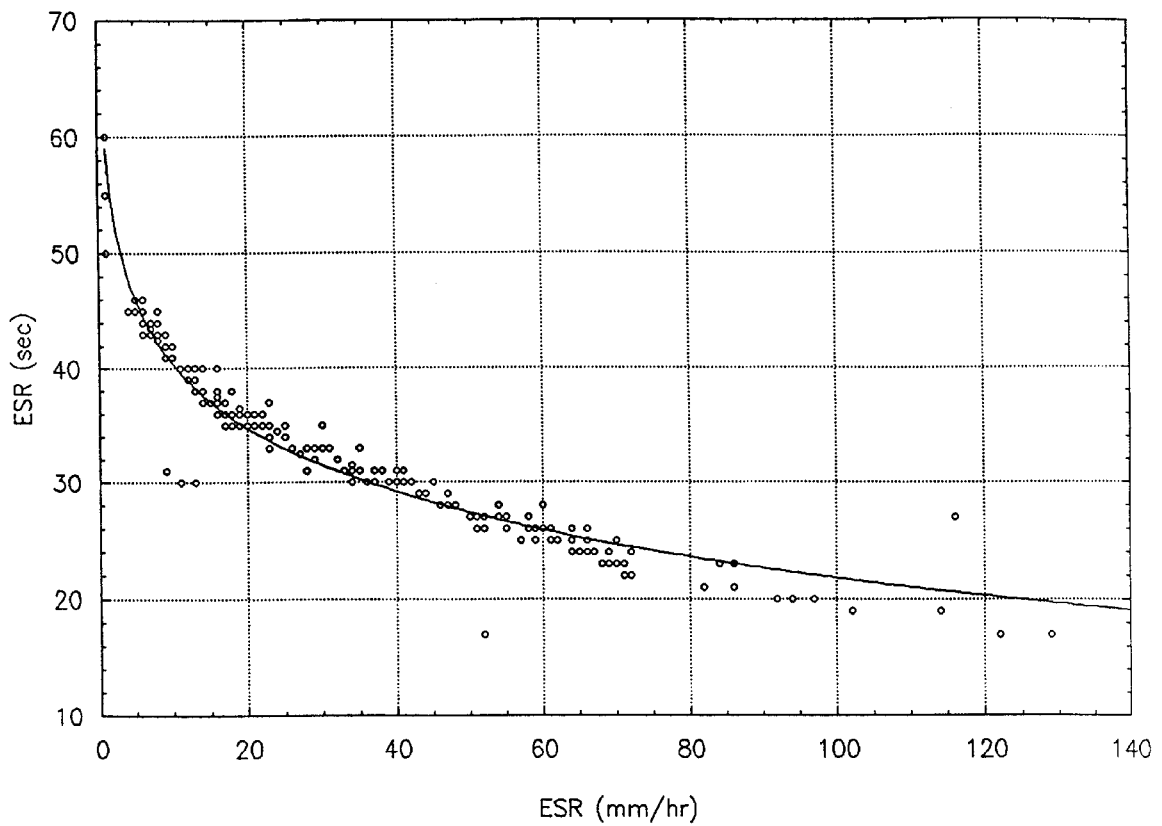
FIG. 9 is a chart of ESR expressed as time (sec) to formation of the cell/plasma interface, plotted against ESR in millimeters per hour measured by traditional technique.

The best fit curve depicted in FIG. 9 is valid for the particular apparatus employed. Consequently, if an operator were using the same apparatus, it is only necessary for him to centrifuge blood until the terminal interface ($I_t$) is formed, record the elapsed time for centrifugation, locate the time on the best fit curve (BFC) and read downwardly to determine the erythrocyte sedimentation rate in millimeters per hour. This could also be done instrumentally.

The above described method represents a simple and quicker alternative to the standard modified Westergren method and may be employed with plastic or glass tubes or other containers containing thixotropic gel, or gel-free tubes or other containers, since the interface formation takes place before the red cells penetrate the gel separation layer.

The same general technique may be employed to ascertain hematocrit (HCT) as is used for ascertaining erythrocyte sedimentation rate (ESR). In determining hematocrit, instead of measuring the elapsed time it takes to form the terminal interface It, the quantity of separated red blood cells is measured. As stated above, hematocrit (HCT) or packed red blood cell volume is the ratio of the volume of the red blood cells to the volume of the whole blood from which the cells were separated. It may be expressed as a percentage or as a decimal fraction.

When our technique is employed using the circular rotor 4 as the container for the whole blood being centrifuged, the video camera 6 initially records the location of the circular edge 35 of the whole blood, i.e. its radial distance from the axis of rotation α of the rotor. After centrifugation, the video camera measures the location of the terminal interface $I_t$ radially from the axis of rotation α.

Since hematocrit (HCT) is defined as the volume of the red blood cells divided by the volume of the whole blood from which it was separated, hematocrit maybe calculated as follows: The distance from the axis α (see FIG. 6b) to the circular inner wall 30 of the rotor 4 is known. The distance from the axis α to the interface $I_t$ (see FIG. 8b) is measurable and the distance from the axis α to the original circular edge of the whole blood 35 is measurable. Under ideal circumstances, the HCT would be directly calculable to the two measured distances. The numerator of the fraction would be the distance from axis α to the wall 30 minus the distance from the axis α to the terminal interface $I_t$. The denominator would be the distance from the axis α to the wall 30 minus the distance from the axis α to the edge 35 of the whole blood. This, however, is only true if the interior of the rotor 4 were uniform, but as will be seen in FIG. 4, it is not. Accordingly, the result must be adjusted by a constant or a formula to correct for the irregular configuration. This could lead to complex mathematical calculation.

Another way to compensate for this irregularity is to print on the rotor 4 as seen in FIG. 2 a series of concentric rings $R_1, R_2, R_3$, etc. which are representative of constant volumes of the interior of the rotor. For example, the rotor's volume may be designated in tenths by printing on its surface ten concentric rings $R_1$, to $R_{10}$. The rings would not be uniformly spaced per se. Their spacing would be determined by the mathematical formula of the internal value of the rotor divided successively by tenths.

Figure 10:
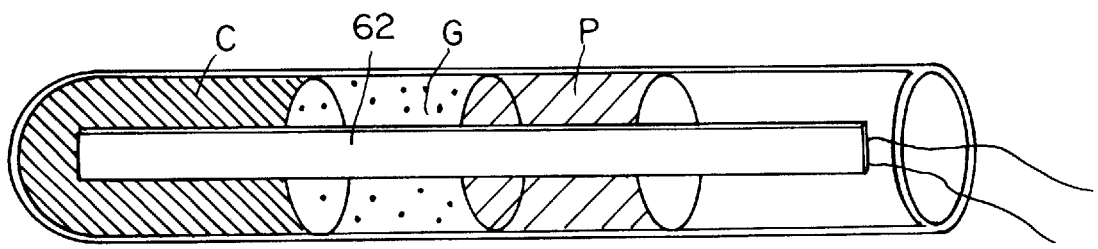
FIG. 10 is a schematic view of a blood separation tube equipped with an optical sensor (after centrifugation).
Figure 11:
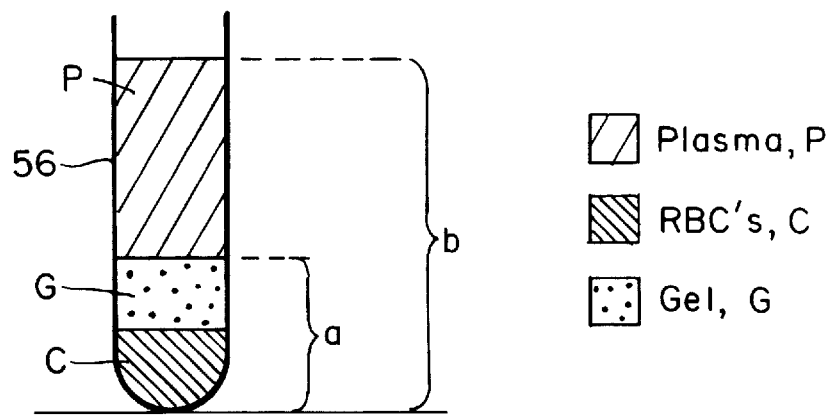
FIG. 11 depicts one type of a blood separator tube after centrifugation where the red blood cells penetrated thixotropic gel in the tube.
Figure 12:
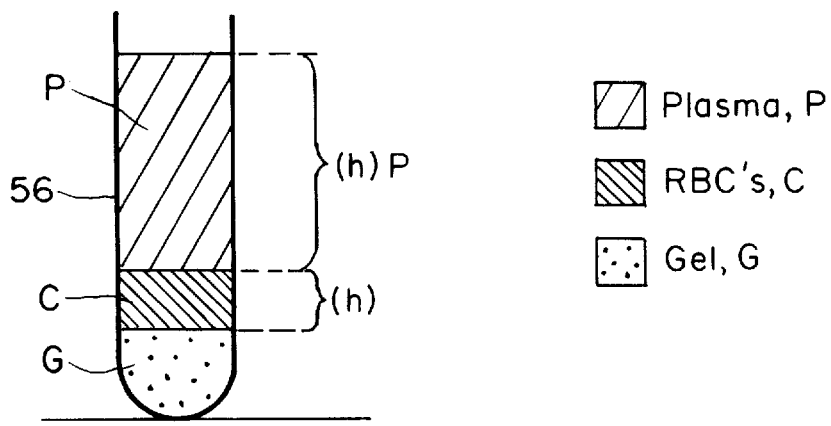
FIG. 12 is a view similar to FIG. 10 after centrifugation where the red blood cells have not penetrated the gel.

A preferred technique, however, is to employ a modified bucket-type centrifuge where the sample containers 56 are conventional commercially available blood centrifuging test tubes of constant diameter and pre-loaded with a quantity of thixotropic gel G (FIGS. 10 and 12). The test tube 56 containing a sample of blood (collected in the presence or absence of an anticoagulant) is placed in the centrifuge 50 (to be described in greater detail hereinafter). As seen in FIG. 11, after centrifugation, the red blood cells C penetrate the gel G and collect at the base of the test tube. The hematocrit is calculated as follows:

$$H_{ct} = \frac{a-c}{b-c}$$

where c is a constant representing the height of the gel G.

Alternatively, the above calculation could be based upon the relative heights of the red blood cells and the plasma measured before the red blood cells C penetrate the gel G as seen in FIG. 12. The formula would then be:

$$H_{ct} = \frac{(h)C}{(h)C + (h)P}$$

Expressed alternatively, HCT is the height of the red blood cells divided by the height of red blood cells plus height of plasma, ignoring the gel. Another alternative way of expressing the result is the sum of the heights of red blood cells and height of gel divided by the collective height of the plasma, the red blood cells and the gel.

Figure 13:
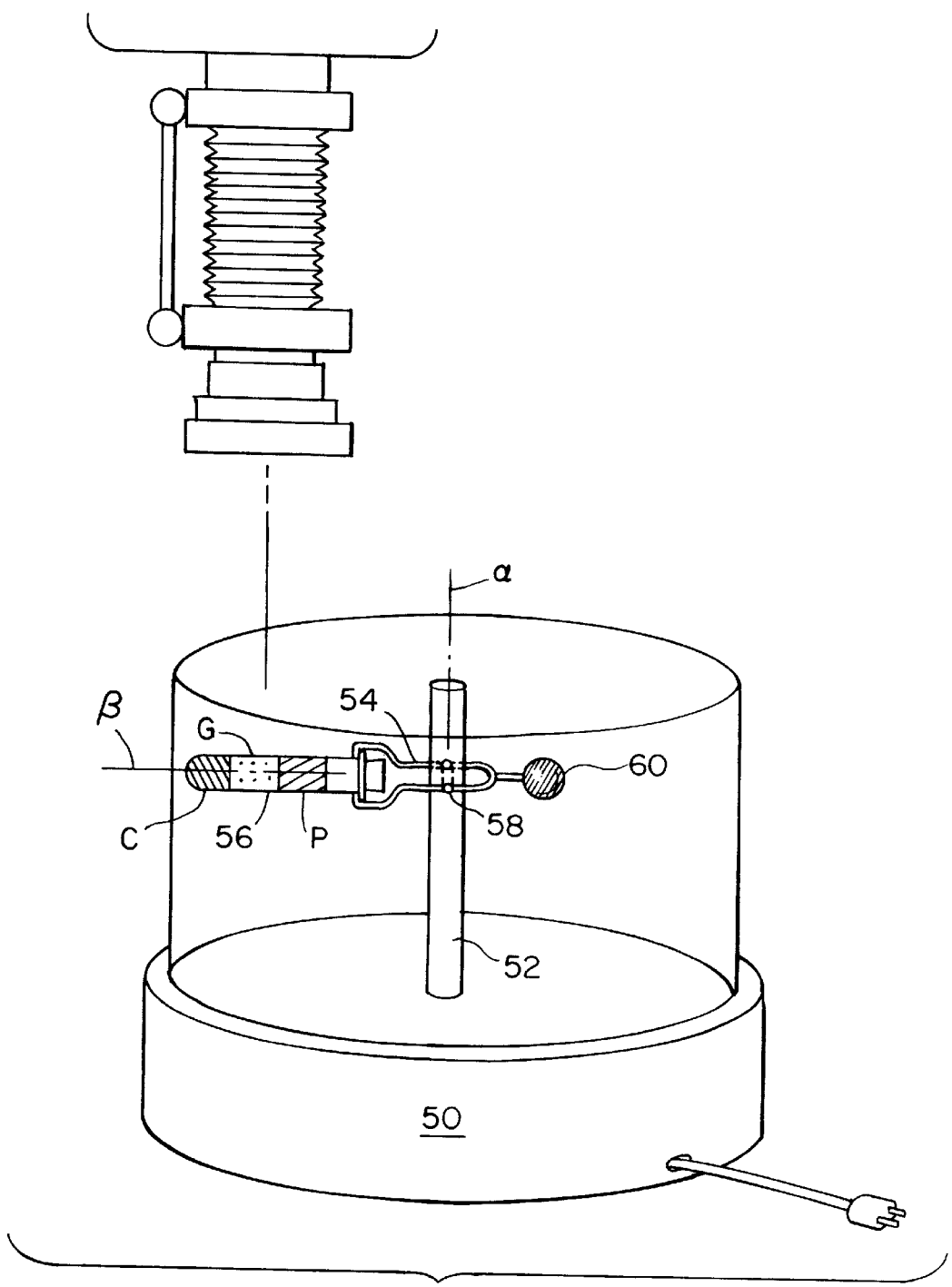
FIG. 13 is a schematic view of another embodiment of the centrifuge.

FIG. 13 is a schematic diagram of a centrifuge employing a conventional integrated serum separated tube style of the type sold under the trade name CORVAC by Sherwood Medical, St. Louis, Mo. for performing the techniques described with reference to FIGS. 11 and 12. The centrifuge may be positioned below the video camera 6 of the type shown in FIG. 1. It has a base 50 and an upstanding rotor shaft 52. A gimbel 54 is pivoted at 58 on the rotor shaft 52. The separator tube 56 is gripped by a clamp of the gimbel 54. A counterweight 60, if needed, may also be pivotally mounted on the rotor shaft 52. The centrifuge is rotated at 3500 RPM for about three minutes. During centrifugation, the separator tube 56 being mounted by the gimbel 54 attains a horizontal position that is indicated by the dotted line β in FIG. 13 whereupon it is in the best possible position to be photographed by the video camera 6, i.e. with the tube 56 at right angles to the axis of the lens of the video camera.

The video camera measures and records the distance from the bottom of the separator tube 56 to the gel/plasma interface designated a in FIG. 11. It also measures distance from the bottom of the tube 56 to the plasma air interface designated b in FIG. 10. The same type of measurement would apply to FIG. 12.

The HCT measurement can be performed separately or following the sedimentation rate determination described above since the sedimentation rate is ascertained in the first 20 to 45 seconds of centrifugation.

Another possible embodiment is disclosed in FIG. 10 wherein the separator tube 56, which would be centrifuged by apparatus similar to that shown in FIG. 13, would include an optical source and sensor 62 associated with the tube. Lead wires 64, 66 would lead to a microprocessor (not shown) which would continuously feed data to the tape and the video monitor 24, or other means of detecting the interface formation by its optical properties. By use of this technique, the video camera and strobe are eliminated and a plurality of separated tubes could be centrifuged simultaneously and the results recorded simultaneously.

The invention claimed is:

1. A method of determining, by centrifugation, the erythrocyte sedimentation rate (ESR) expressed in conventional Westergren ESR methodology terms and units (mm/hr), of a specific sample of whole blood, comprising the steps of:
   A) comprising the sub-steps of:
      a) obtaining a plurality of samples of whole blood;
      b) dividing the samples into two portions each;
      c) centrifuging a first portion of each sample;
      d) forming an interface between the erythrocytes and the fluid portion of the first portion of each sample; and
      e) determining the interface time in seconds by measuring the elapsed time from initiating centrifugation to the formation of the interface in the first portion of each sample;
   B) determining the erythrocyte sedimentation rate of the second portion of each sample in conventional Westergren terms and units (mm/hr) by employing conventional Westergren technique;
   C) comprising the sub-steps of:
      a) creating a plot comprising the elapsed time (seconds) of forming the interface of the first portion of each sample (interface time) plotted on one axis against the erythrocyte sedimentation rate of the second portion of each sample determined by conventional Westergren technique (mm/hr) plotted on a second axis; and
      b) creating a line of best fit of the points on the plot represented by data on both axes;
   D) comprising the sub-steps of:
      a) obtaining a specific sample of the whole blood desired to be tested;
      b) centrifuging the specific sample;
      c) forming an interface between the erythrocytes and the fluid portion of the specific sample;
      d) determining the interface time (seconds) by measuring the elapsed time from initiating centrifugation to the formation of the interface of said specific sample; and
   E) expressing the erythrocyte sedimentation rate of the specific sample in conventional Westergren ESR methodology terms and units (mm/hr) on the second axis by reading the point that corresponds to the elapsed time (seconds) on the first axis of the plot derived per C.c. above.

2. Method according to claim 1, wherein the step of measuring is optical.

3. Method according to claim 1, wherein the step of measuring is by video camera photography.

4. Method according to claim 1, wherein the step of measuring includes the steps of recording the time of the formation of the interface and analyzing the recording optically.

5. A method of determining, by centrifugation, the erythrocyte sedimentation rate expressed in conventional Westergren ESR methodology terms and units (mm/hr) of a specific sample of whole blood comprising the steps of:
   A) comprising the sub-steps of:
      a) obtaining a specific sample of the whole blood desired to be tested;
      b) centrifuging the specific sample;
      c) forming an interface between the erythrocytes and the fluid portion of the specific blood sample; and
      d) measuring the elapsed time (interface time) in seconds from initiating centrifugation to the formation of the interface;
   B) expressing the erythrocyte sedimentation rate of the specific sample in conventional Westergren ESR methodology terms and units (mm/hr) comprising the sub-steps of:
      a) locating the interface time of the specific sample as determined in Step A on one axis of a previously made, best fit, plot derived from testing a plurality of samples of whole blood in which the interface time of each sample was plotted on a line of best fit against the Westergren sedimentation rate (mm/hr) obtained from the same plurality of samples; and
      b) reading the corresponding erythrocyte sedimentation rate (mm/hrs) in conventional Westergren ESR methodology terms from the second axis.

6. Method according to claim 5, wherein the step of measuring is optical.

7. Method according to claim 5, wherein the step of measuring is by video camera photography.

8. Method according to claim 5 wherein the step of measuring includes the steps of recording the time of the formation of the interface and analyzing the recording optically.

* * * * *